United States Patent [19]

Bell, Jr. et al.

[11] 4,136,557
[45] Jan. 30, 1979

[54] PANTY HOSE TESTING APPARATUS AND METHOD

[75] Inventors: Cecil R. Bell, Jr., Pinnacle; Walter R. Sizemore, Winston-Salem, both of N.C.

[73] Assignee: Hanes Corporation, Winston-Salem, N.C.

[21] Appl. No.: 871,086

[22] Filed: Jan. 19, 1978

[51] Int. Cl.² .............................................. G01N 3/00
[52] U.S. Cl. ..................................... 73/816; 33/2 A; 73/835; 73/840; 73/159; 223/61; 223/77
[58] Field of Search ........................... 73/95–97, 73/102–103, 159; 26/70; 33/2 A; 223/61, 74, 75, 77

[56] References Cited

U.S. PATENT DOCUMENTS

| | | | |
|---|---|---|---|
| 2,065,372 | 12/1936 | Johnston | 223/61 |
| 2,369,661 | 2/1945 | Dangelmajer | 73/159 |
| 2,675,703 | 4/1954 | Hemmerich et al. | 73/159 |
| 3,039,299 | 6/1962 | Roof | 73/96 |
| 3,285,056 | 11/1966 | Mattivi | 73/102 X |
| 3,471,068 | 10/1969 | Foreman | 223/61 |
| 3,639,987 | 2/1972 | Page | 33/2 |
| 3,750,291 | 8/1973 | Foreman | 33/2 A |
| 3,879,990 | 4/1975 | Joy | 73/95 |

Primary Examiner—Charles Gorenstein
Attorney, Agent, or Firm—Charles Y. Lackey; William S. Burden

[57] ABSTRACT

A panty hose testing apparatus in which a manikin conforming substantially to the lower portion of a human torso is provided with waist, leg, and hip portions for receiving thereon panty hose garments and the like. The garment is retained upon the manikin, during testing, by opposed clamp assemblies which engage the garment and manikin adjacent the waist portion, and a crotch member is displaceable longitudinally of the leg portions and applies a force to the crotch area of the garment sufficient to initiate seam damage or a tear in the garment fabric. A gauge measures the force necessary to initiate damage to the garment.

10 Claims, 7 Drawing Figures

PANTY HOSE TESTING APPARATUS AND METHOD

BACKGROUND, BRIEF SUMMARY AND OBJECTS OF THE INVENTION

The invention relates generally to the testing of garments, and more particularly to a system for measuring the resistance of panty hose garments and the like to fabric and seam damage in the body portion of the garment.

A common type of panty hose garment includes two tubular stocking members which have been slit and seamed together in the upper portion to form a substantially U-shaped seam in the crotch and waist portions and with an elastic band sewn to or knit integrally in the garment waist portion. Alternatively, a crotch insert may be sewn in between the two legs of the garment at the lower extermities of the crotch or the crotch insert may extend from the front to the back of the garment as a fully shaped panel.

Various prior art forms have been used for inspecting, measuring and sizing panty hose garments. However, there are no known techniques or devices available for testing or indicating damage resistance of the seams or fabric in the body portion of the garment.

The present invention includes a manikin conforming to the lower portion of a human torso which is adapted to receive a panty hose garment. The garment is clamped to the manikin adjacent the waist portion, and a crotch member is displaceable longitudinally of the manikin for applying a progressively increasing force to the crotch area of the garment. A gauge is provided to indicate the initial force required to penetrate the fabric, start a tear, or damage the seams in the garment crotch area. By applying forces to the body portion of the garment, it is possible to determine whether like garments come within prescribed standards or requirements.

One of the primary objects of the invention is the provision of a means for testing a panty hose garment resistance to seam damage or fabric damage in the body portion.

Another object of the invention is the provision of a system of testing, wherein the force required to initiate a tear can be recorded.

Other objects and advantages of the invention will become apparent when considered in view of the following detailed description.

DETAILED DESCRIPTION OF THE INVENTION

Figure 1:
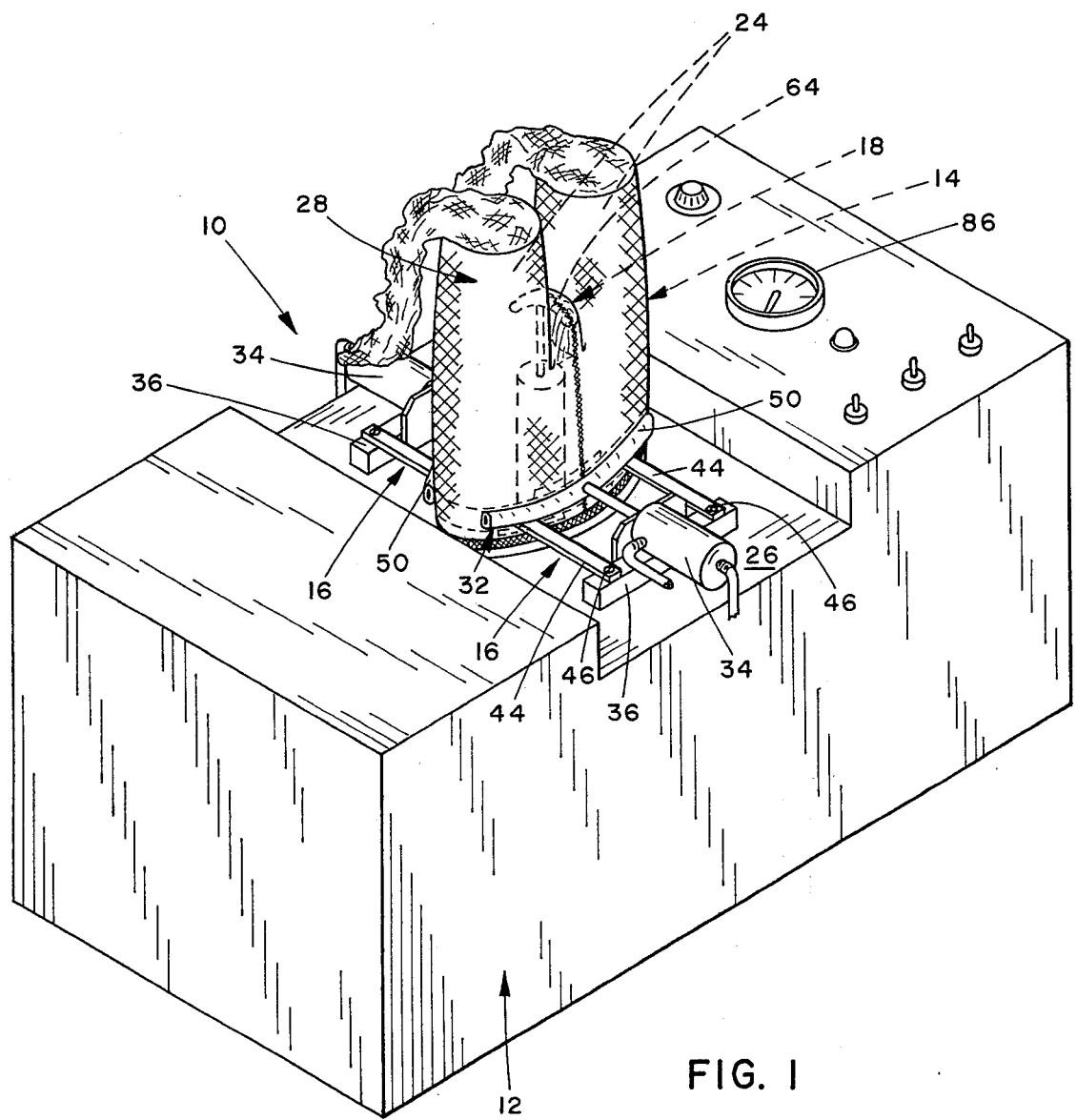
FIG. 1 is a perspective view of testing apparatus of the present invention, and illustrating a panty hose garment positioned upon a manikin with the crotch member in an elevated position.
Figure 2:
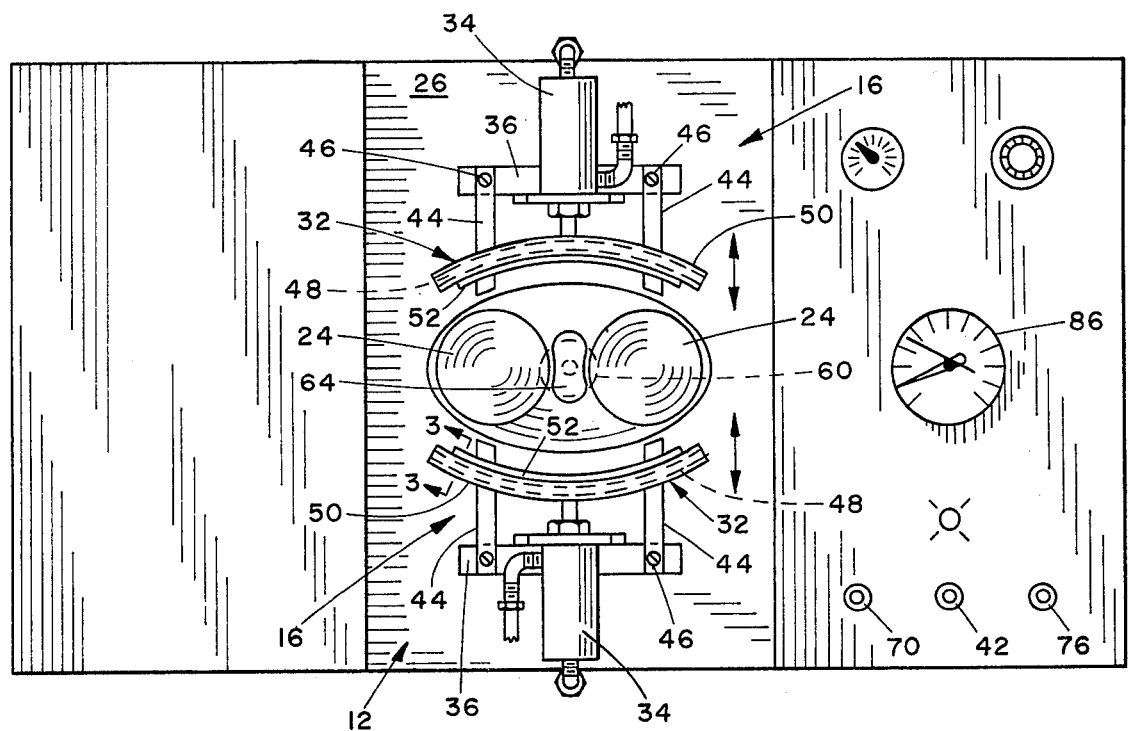
FIG. 2 is an enlarged top plan view of the fabric testing apparatus of the present invention prior to receiving a garment, and illustrating the clamps in opened positions.

Referring to the drawing, and particularly to FIG. 1, the testing apparatus 10 includes a support structure 12, a manikin 14, opposed clamping assemblies 16 and a crotch member assembly 18.

The support structure 12 may include a housing or cabinet, as shown, for supporting the various components of the testing apparatus, or may comprise an open type framework, table, or other suitable means.

Figure 4:
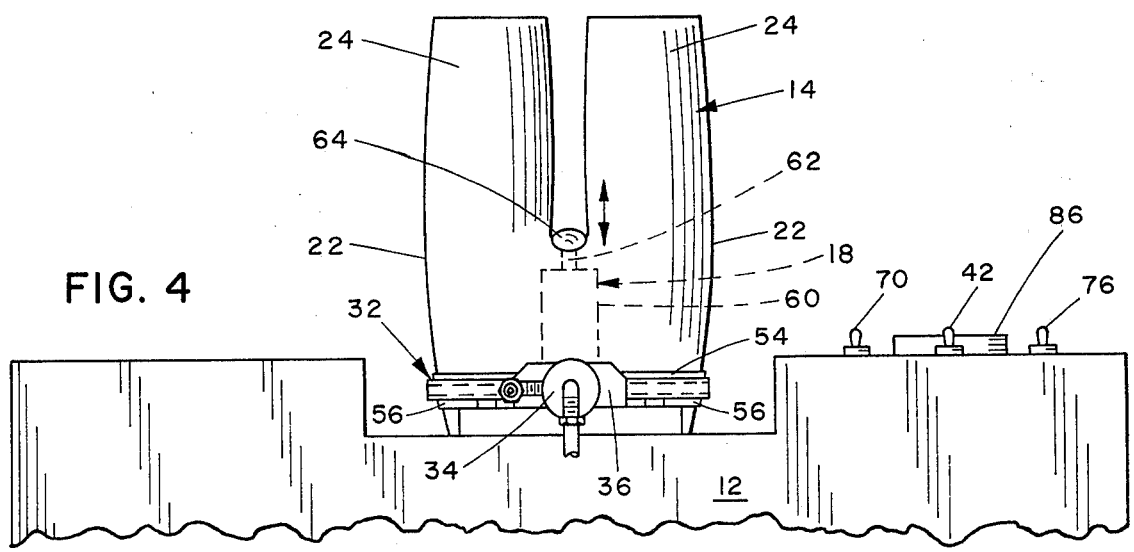
FIG. 4 is a fragmentary, front elevational view of the apparatus FIG. 1 with the crotch member in the lower most position.

Referring to FIG. 4, the manikin 14 has an external configuration which conforms substantially to the lower portion of a human torso. The manikin includes a waist portion 20, hip portions 22, and at least segments of spaced legs 24. The leg segments 24 are spaced in generaly parallel relation. While leg segments 24 have been illustrated, it is to be understood that the manikin also may include complete, spaced parallel leg and foot portions, if desired. The manikin 14 is secured to the support structure 12, in a conventional manner, not shown, with the manikin waist portion abutting the upper surface 26 of support 12.

Figure 5:
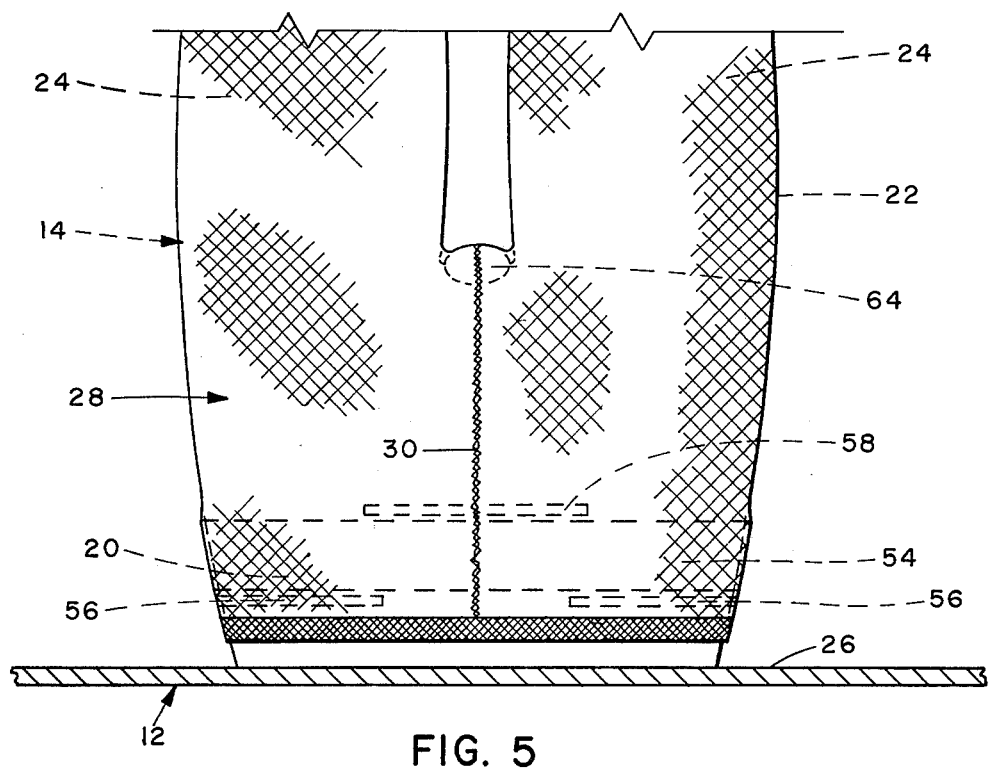
FIG. 5 is a fragmentary, front elevational view of the manikin having a garment positioned thereon and illustrating the friction means for facilitating retention of the garment upon the manikin.

The manikin 14 is adapted to receive a panty hose garment 28 thereon for testing, as illustrated by FIGS. 1 and 5. The garment 28 may be of tube type construction or may be formed from stocking materials slit and sewn together, in a conventional manner, forming a garment having a U-seam 30, FIG. 5. Alternatively, the garment may be provided with a gusset, not shown.

A pair of opposed clamping assemblies 16 are provided for retaining a garment 28 upon the manikin 14 while being tested. Each clamping assembly includes a generally arcuate clamp 32 displaceable by a double acting fluid cylinder 34 between a position engaging the waist portion 20 of the manikin and a position spaced from the manikin for permitting a garment 28 to be readily placed upon or removed from the manikin 14.

Each of the fluid cylinders 34 is attached to a bracket 36 which is mounted upon support 12. The cylinders 34 are operated simultaneously by a fluid system including a valve 38 controlled by associated solenoid 40 to move the cylinder piston rods and the clamps 32 into engagement with the manikin waist portion 20 and to retract clamps 32 from the manikin. The solenoid 40 is controlled by a switch 42 positioned upon the support 12.

A pair of elongated, general horizontally disposed guides 44 are secured adjacent one end by fasteners 46 to each of brackets 36 and extend towards the manikin waist portion. The guides retain the clamps 32 in a generally horizontal plane as they are displaced by fluid cylinders 34.

Figure 3:
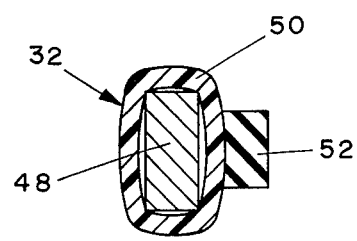
FIG. 3 is a cross-sectional view taken along 3—3 of FIG. 2.

Each clamp 32 includes an arcuate metal bar 48, FIG. 3, encompassed by a plastic tube 50 are provided on the forward edge with a strip of rubber 52 or other suitable frictional material. The plastic tubes 50 prevent damage to the garment when clamped. The tubes 50 and rubber strips 52, cooperate with a rubber band 54 and spaced rubber strips 56, 58 secured to the manikin 14 adjacent the waist portion to retain a garment in position and prevent movement of the waist portion when the crotch member assembly is actuated. Strips 56 are provided at the sides of the manikin and below the band 54 while strips 58 are provided at the front and back of the manikin and above band 54. The strips 52, 56, 58 and band 54 may be of suitable materials, other than rubber, for preventing movement of the garment waist position relative to the manikin waist portion when gripped by clamps 32.

The crotch member assembly 18 includes a double acting fluid cylinder 60 fixedly secured in a generally vertically disposed manner by suitable fasteners, not shown, to the support structure 12. Attached to the outer end of the piston 62 of the cylinder 60 is a crotch member 64. The crotch member 64 is positioned intermediate the leg segments 24 and has an elongated, arcuate configuration generally conforming to the contour of the manikin. The edges of the member 64 are dull or rounded to prevent damage to the garment. Normally, the crotch member is positioned in abutting relation with the manikin, as shown by FIGS. 4 and 5, and is capable of being extended generally vertically upwardly by piston 62 as shown by FIG. 1 for testing the crotch area of a garment positioned upon a manikin by stretching the garment seams and fabric until a break is initiated.

The double acting fluid cylinder 60 is controlled through a valve 66 operated by an associated solenoid 68. The solenoid 68 in controlled by a switch 70.

Figure 6:
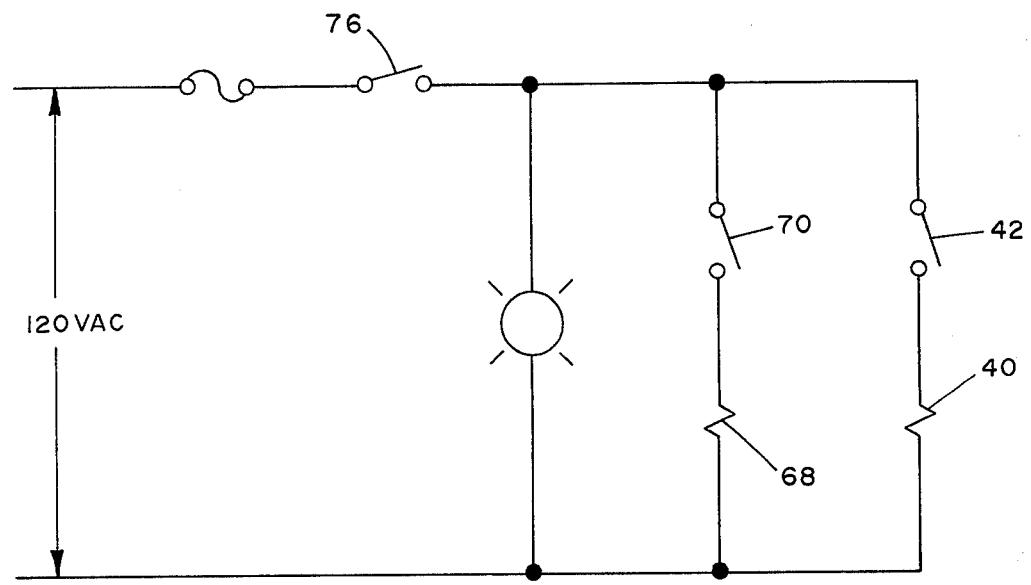
FIG. 6 is a schematic electrical diagram for the testing apparatus.
Figure 7:
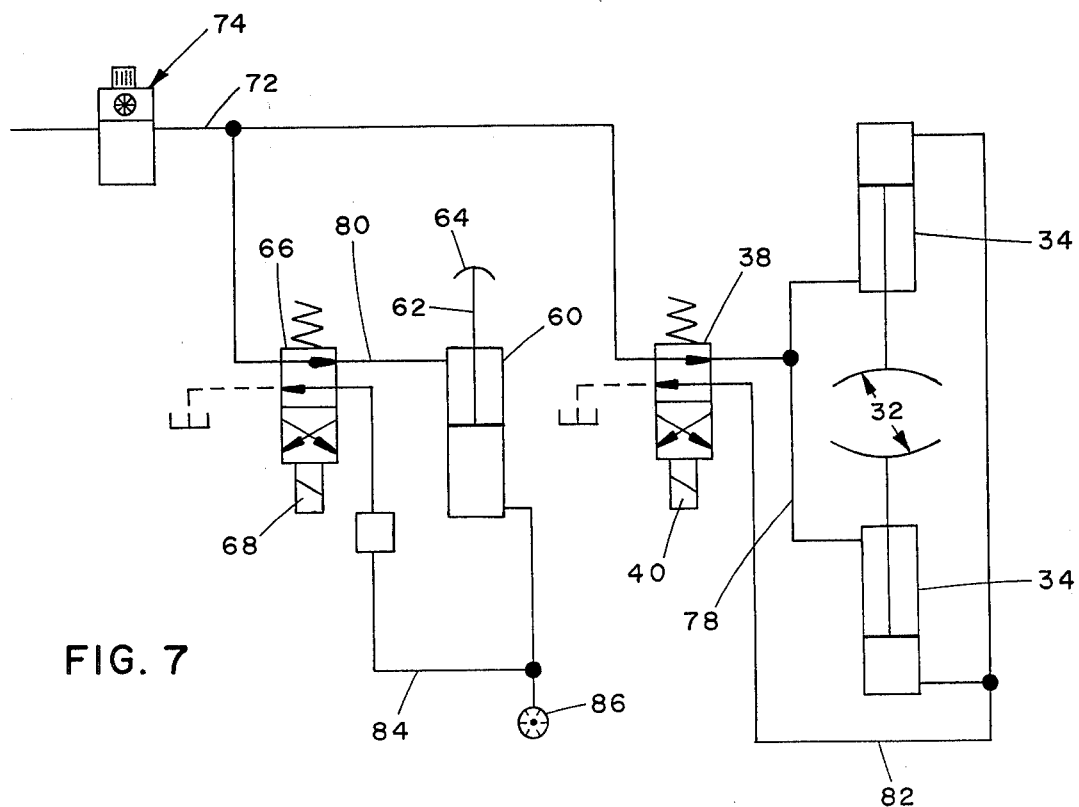
FIG. 7 is a pneumatic diagram for controlling the clamps and displaceable crotch member of the testing apparatus.

In testing garment resistance to seam burst and/or fabric damage, the electrical circuit, FIG. 6, is energized through switch 76 and fluid under pressure is directed to line 72 through regulator filter 74, valves 38, 66, conduit 78, 80 and to cylinders 34 and 60 such that initially the clamps 32 are in the opened positions and the displaceable crotch member 64 is positioned in abutting relation with the manikin crotch area. Actuating of claim switch 42 activates solenoid 40 displacing valve 38 such that the fluid pressure through line 82 closes the clamps 32 and secures the garment adjacent the manikin waist portion. The operator then actuates switch 70 which controls solenoid 68 to shift the valve 66 and fluid pressure is directed through line 84 to the lower end of cylinder 60. The fluid pressure displaces piston 62, urging the member 64 upwardly or away from the manikin. The crotch member 64 presses against the crotch area of a garment clamped upon the manikin 14 and the member 64 continues to move away from the manikin body portion until such time that the garment is damaged. The gauge 86 records the force necessary to burst a garment seam or otherwise damage the garment, and gives an indication of the resistance or force comparable garments will afford to forces tending to damage the garment. Upon observation by the operator of seam or fabric damage, the switch 70 again is actuated to retract the piston 62. The gauge 86 may include an indicator which is displaced as the pressure is line 84 increases, and which remains in the maximum pressure position for initiating damage until being reset to zero by an operator.

We claim:

1. In an apparatus for testing the resistance to fabric or seam damage to panty hose garments and the like; a manikin having an external configuration substantially conforming to the lower portion of a human torso and including waist, hip, and leg portions, crotch means including a crotch member intermediate the leg portions, said crotch member normally positioned in substantially abutting relation with said manikin, means adjacent said manikin waist portions for applying a force to a garment for firmly holding a garment upon said manikin, and means for selectively applying a force to said crotch means to displace said crotch member relative to said leg portions and against the crotch portion of a garment sufficiently to initiate a tear or seam damage to the garment material, and means for recording the force applied by said crotch means sufficient to initate seam or fabric damage of the garment.

2. In apparatus as recited in claim 1, said means applying a force to said crotch means including fluid means for displacing said member away from said manikin and longitudinally of said legs for applying a force against the crotch portion of a garment positioned upon said manikin.

3. In an apparatus as recited in claim 2, said means for holding a garment upon said manikin including at least one assembly for clamping the garment adjacent said manikin waist portion.

4. In an apparatus as recited in claim 3, said assembly for clamping the garment to said manikin including a first displaceable member provided with a gripping surface having a high coefficient of friction for engaging and clamping the garment adjacent the waist portion to said manikin.

5. In an apparatus as recited in claim 3, wherein a plurality of assemblies are provided for clamping the garment.

6. In an apparatus as recited in claim 4, wherein at least a portion of the waist portion of said manikin is provided with a gripping surface having a high coefficient of friction for cooperating with said first displaceable member gripping surface.

7. In an apparatus as recited in claim 6, said assembly for clamping the garment to said manikin including fluid cylinder means for displacing said first displaceable member between a position spaced from said manikin and a position in clamping engagement with said manikin.

8. In an apparatus as recited in claim 1, said means for retaining a garment upon said manikin including a pair of opposed clamping assemblies, each clamping assembly including an arcuate member provided with a frictional surface for clamping a garment upon said manikin adjacent said wasit portion.

9. In an apparatus as recited in claim 8, said crotch member substantially bridging the gap between said spaced leg portions, said crotch means further including means for displacing and member longitudinally of said leg portion for gradually applying a force to the crotch area of a garment positioned upon said manikin to tear or damage the garment fabric, said force indicating means including a gauge for recording fluid pressure.

10. The method of determining the resistance to seam damage of the crotch portion of a panty hose garment comprising; increasing the volume or capacity of the panty hose garment to correspond generally to the volume of a wearer by positioning the garment upon a manikin of a desired size, clamping the panty hose garment to the manikin by applying selected forces adjacent the waist portion of the garment, displacing the garment crotch portion relative to the manikin by applying a progressively increasing force to the panty hose crotch portion longitudinally of the garment leg portions and outwardly of the manikin while continuously applying the forces to the garment waist portion, and measuring the force required to initiate seam or fabric damage to the panty hose garment.

* * * * *